United States Patent [19]

Kambara et al.

[11] Patent Number: 5,051,162

[45] Date of Patent: Sep. 24, 1991

[54] FLUORESCENCE DETECTION TYPE ELECTROPHORESIS APPARATUS AND ITS SUPPORTING VESSEL

[75] Inventors: Hideki Kambara, Hachioji; Keiichi Nagai, Higashiyamato, both of Japan

[73] Assignee: Hitachi, Ltd., Tokyo, Japan

[21] Appl. No.: 505,325

[22] Filed: Apr. 5, 1990

[30] Foreign Application Priority Data

Apr. 12, 1989 [JP] Japan ............................... 1-90842

[51] Int. Cl.⁵ ............................................. G01N 27/26
[52] U.S. Cl. ............................ 204/299 R; 204/182.8; 250/458.1; 250/461.1; 250/461.2; 356/344
[58] Field of Search ............. 204/180.1, 182.8, 299 R; 250/458.1, 459.1, 461.1, 461.2; 356/344

[56] References Cited

U.S. PATENT DOCUMENTS

| | | | |
|---|---|---|---|
| 3,980,540 | 9/1976 | Hoefer | 204/299 R |
| 4,325,796 | 4/1982 | Hoefer et al. | 204/182.8 |
| 4,832,815 | 5/1989 | Kambara et al. | 204/299 R |
| 4,881,812 | 11/1989 | Ohkubo et al. | 356/344 |

OTHER PUBLICATIONS

"Nature", vol. 321, pp. 674-679 (1986).

"Bio/Technology", vol. 6, pp. 816-821 (1988).

Primary Examiner—T. Tung
Assistant Examiner—David G. Ryser
Attorney, Agent, or Firm—Pennie & Edmonds

[57] ABSTRACT

A fluorescence detection type electrophoresis apparatus comprising an excitation laser beam source (1, 29), fluorescent light detector portion, and electrophoresis separation device which can measure many samples at the same time in such a way that it has a plurality of slab gels (4, 23) being provided in parallel and a fluorescent light detector (8, 32) installed in position where it can individually and simultaneously receive and detect fluorescent lights coming out of migration direction lower ends (16, 40) of the slab gels (4, 23) or of portions adjacent thereto. It is preferable that the fluorescence detection type electrophoresis apparatus has a plurality of slab gels (4, 23) integrated together via gel supporting plates (22). For this, a supporting vessel for use with the fluorescence detection type electrophoresis apparatus can be used for effective preparation of numbers of slab gels (4, 23), in which a plurality of vertically oriented gel supporting plates (22) is arranged at predetermined intervals on the bottom thereof.

9 Claims, 4 Drawing Sheets

FLUORESCENCE DETECTION TYPE ELECTROPHORESIS APPARATUS AND ITS SUPPORTING VESSEL

BACKGROUND OF THE INVENTION

This invention relates to a fluorescence detection type electrophoresis apparatus. More particularly, it relates to a fluorescence detection type electrophoresis apparatus suitable to separate and detect DNA, RNA, or protein labeled by fluorophore.

A conventional technique used for determining a DNA base sequence was autoradiography. A more simple optical detection technique has been recently used with fluorescence label (as disclosed for example in "Nature", vol. 321, pp 674–679 (1986); "Bio/Technology", vol. 6, pp 816–821 (1988); and, U.S. Pat. No. 4,832.815. With this method, fluorescence-labeled DNA fragments are migrated in slab gels of about 20 by 40 cm each. A laser beam is thrown on the downstream at a certain distance around 20 cm from the start of migration. A detector is placed around right angles to the migration direction, that is, in front of the slab gels, to receive the fluorescent light from the fluorescence-labeled DNA fragments passing through the slab gels. The length of the DNA fragment can be known in terms of the migration time of the DNA fragment to determine the DNA base sequence.

An apparatus realized in the conventional technique mentioned above needs one measuring instrument for one electrophoretic plate, so that the single measuring instrument cannot obtain information from a plurality of electrophoretic plates. The technique is inappropriate in that a number of apparatuses are needed to measure many samples. The technique also is inappropriate for measuring many samples simultaneously since it is limited by the number of migration lanes to be kept on the single electrophoretic plate.

SUMMARY OF THE INVENTION

It is an object of this invention to solve the problems mentioned above, that is, to provide a fluorescence detection type electrophoresis apparatus and its supporting vessel in which a single measuring instrument can obtain information from a plurality of electrophoretic plates simultaneously and are appropriate for measurement of many samples.

In order to realize the above-mentioned object, the fluorescence detection type electrophoresis apparatus according to the present invention comprises at least (1) an electrophoresis separation device, (2) an excitation laser beam source for generating fluorescent light by exciting the fluorophore which labels the sample, and (3) a fluorescent light detector portion for detecting the generated fluorescent light, and is characterized in that a plurality of slab gels are provided in parallel, and a fluorescent light detector is installed in position where it can individually and simultaneously receive and detect fluorescent lights outputed from migration direction side ends of the slab gels or from portions adjacent thereto which the laser beam emitted from the excitation laser beam source irradiates.

A preferred embodiment of the fluorescence detection type electrophoresis apparatus according to the present invention in relation to installation position of the fluorescent light detector, has a light receiver of the fluorescent light detector provided in position facing to the lower ends of the slab gels arranged in parallel. For more detail of the embodiment, referring to now FIG. 1, lower portions of the slab gels arranged in parallel are positioned within a lower buffer vessel which is transparent, and the light receiver of the fluorescent light detector is provided opposite to a bottom of the lower buffer vessel. As another exmaple, additional mirrors can be arranged so that they can reflect fluorescent lights output from the lower ends of the slab gels or from the portions adjacent thereto to come into the light receiver of the fluorescent light detector. It is possible to use a one-dimensional or two-dimensional fluorescent light detector as the fluorescent light detector mentioned above.

In addition, it is preferable that in the fluorescence detection type electrophoresis apparatus according to the present invention, means is provided to irradiate the lower end of each slab gels arranged in parallel or the portion adjacent thereto with light, at the same time at least within the same slab gel, and the fluorescent light detector has an optical system that can receive a plurality of fluorescent light images simultaneously.

The portion adjacent to the lower end of each slab gels that is mentioned above, refers to a portion that the fluorescent light coming out of the slab gel with irradiation of light thereto can be fully detected at the same time by the fluorescent light detector. The adjacent portion can be determined by a simple experiment.

Another preferred embodiment of the fluorescence detection type electrophoresis apparatus according to the present invention, as illustrated in FIGS. 4 through 6, can have a plurality of slab gels integrated together via gel supporting plates. The gel supporting plate can be made of glass plate, quartz plate, or the like. It may be non-transparent. This allows for a wide freedom for selecting a material. For example, using a material having a high heat conduction, such as silicon carbide (SiC), can provide a high heat radiation.

The slab gel for use in the fluorescence detection type electrophoresis apparatus according to the present invention can have 20 to 30 sample injection wells formed. These have fluorescence-labeled samples injected therein. As the slab gels are preferably available polyacrylamide gel of 4 to 8% or agarose gel of 0.3 to 1%. It should be noted that the concentration of the polyacrylamide is hereinafter indicated as its total monomer concentration which is represented by percentage of weight per volume (g/ml). Also, the concentration of the agarose gel is hereinafter indicated as percentage of weight per volume (g/ml).

As a sample to be used for separation and detection by the fluorescence detection type electrophoresis apparatus according to the present invention can be DNA or RNA of which the base sequence should be determined. It also can use a protein or the like as sample.

A still another preferred embodiment of the fluorescence detection type electrophoresis apparatus according to the present invention with use of a multicolor-fluorescence-labeled sample to be fluorescence-detected, can have means that can disperse by wavelengths the fluorescent lights coming out of the lower ends of the slab gels arranged in parallel or the portions adjacent thereto as interleaved in paths in which the fluorescent lights can be focused on the fluorescent light detector.

In turn, a supporting vessel for use with the fluorescence detection type electrophoresis apparatus is an invention relating to a practical device in which, as described above, the plurality of the slab gels are laminated together with use of the gel supporting plates. As shown in FIGS. 4 and 5, the supporting vessel has a plurality of the gel supporting plates vertically positioned at predetermined intervals on a bottom thereof, and has an injection inlet for unpolymerized acrylamide monomer on a lower portion thereof. On the vertically positioned supporting plates on the supporting vessel, there is a space that can hold electrolyte. In addition, the supporting vessel has a communicating groove on its bottom to allow the unpolymerized acrylamide monomer injected from the injection inlet to flow into between the plurality of the gel supporing plates.

When a light is thrown onto a portion at a certain distance apart from a start point of migration with a pulurality of slab gels arranged in parallel, a fluorescent light can be emitted from that portion. In the conventional technique in which a plurality of fluorescent light images are overlapped as observed at right angles toward the surface of the slab gels, information of individual slab gels cannot be obtained. However, the information can be separately observed if the slab gels are observed toward the side ends in the migration direction.

The fluorescence detection type electrophoresis apparatus of the present invention has a detector such as a high-sensitivity two-dimensional sensor arranged at a position at which each of the fluorescent lights emitted from the lower ends or portions adjacent thereto can be received individually and simultaneously, for example, at a position opposite to the lower ends. Therefore, it allows the single detector to vertically divide and simultaneously detect as line images the fluorescent images from different electrophoretic plates.

Also, the fluorescence detection type electrophoresis apparatus of the present invention can maintain the number of migration lanes same as 'n' times the width of the slab gel if 'n' slab gels are provided. This allows measuring numbers of samples.

In order to detect a wide slab gel using a line sensor, the conventional technique must use a long line sensor or convert the fluorescent image to a small one using a lens having a large contraction power. This results in a technical difficulty in obtaining a high sensitivity. The apparatus of the present invention needs no lens having the large contraction power as it detects numbers of short fluorescent images. This means that it is adequate for obtaining the high sensitivity.

It is very important to make the fluorescent light detection sensitivity high. To achieve high sensitivity needs a high intensity of the light received is required. The received light intensity is proportional to $1/\{1+(1/m)\}^2$ where 'm' is a magnification factor of image. This means that the received light intensity decreases with the image reduced. On the other hand, in order to increase the number of DNA samples to be processed a time, the number of migration lanes must be increased. The width of the migration lane must be made large to make numbers of migration lanes on one electrophoretic plate. The line sensor or two-dimensional sensor having a relatively cheap image intensifier tube has an effetive aperture of 25 mm at most. This is involved in a reduced light reception as the image magnification, 'm', is reduced with measurement of a long fluorescent light image.

The fluorescence detection type electrophoresis apparatus of the present invention divides the long fluorescent light image to two dimensions for detection. It is advantageous in that the image magnifying power, 'm', may not be reduced.

If the slab gels are laminated, this allows arranging the gels at certain intervals, and the number of the gels can be increased as required. A glass plate of 5 mm thick is normally placed between the gels. Even ten sheets of glass plates with slab gel of 5 cm thickness can be used by using the two-dimensional detector without any problem.

In the normal electrophoretic measurement, the slab gel will generate a heat as much as 20 to 30 W per sheet. The current fluorescent light detector is limited to a visual field of about 15 cm by 15 cm. It is therefore preferrable that the number of the slab gels should be ten or less sheets. But, it is possible to use more sheets of slab gels. The interval of adjacent slab gels is preferrably 15 to 20 mm for ten or more sheets, or may be wider for less number of sheets. The laminated slab gel unit can be reduced as narrow as 5 mm or less.

In addition, the fluorescence detection type electrophoresis apparatus of the present invention, as configured above, allows simply fabricating numbers of slab gels in a way that the supporting vessel containing the gel supporting plates has unpolymerized acrylamide monomer injected thereinto.

DESCRIPTION OF THE PREFERRED EMBODIMENTS

First Embodiment

Figure 1:
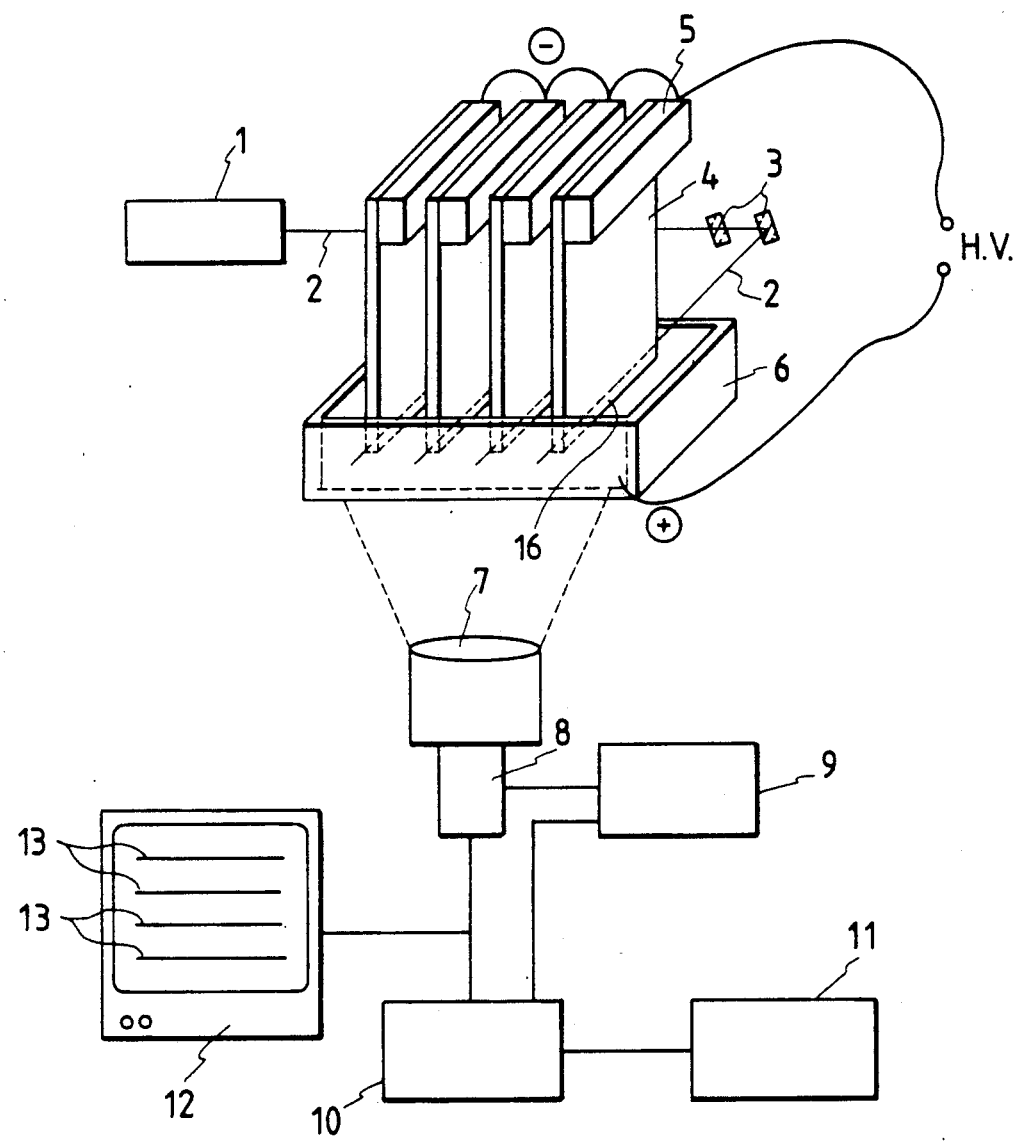
FIG. 1 is a combined block diagram and partial perspective view of the fluorescence detection type electrophoresis apparatus in an embodiment of the present invention.
Figure 2:
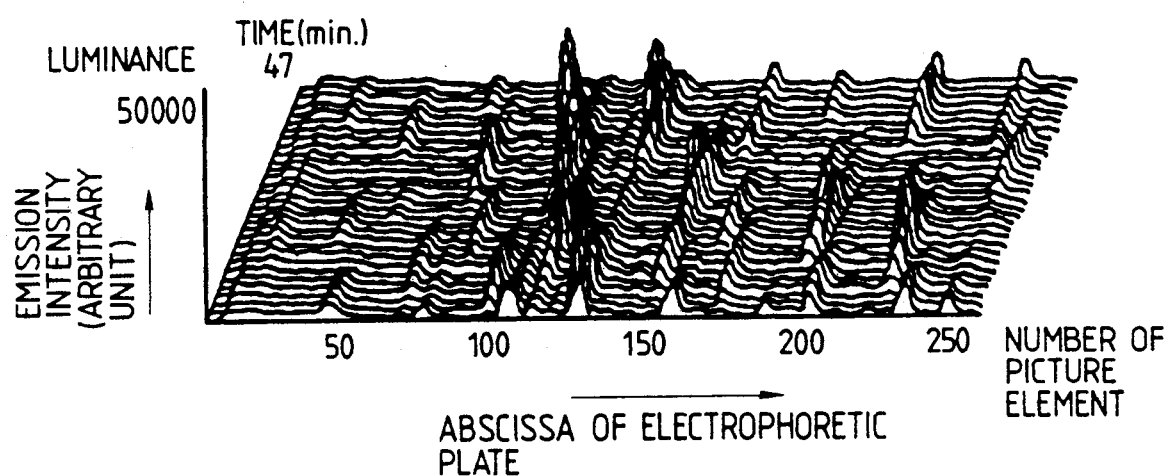
FIG. 2 is a graph illustrating a monitor signal strength varying with time as obtained by the apparatus shown in FIG. 1.
Figure 3:
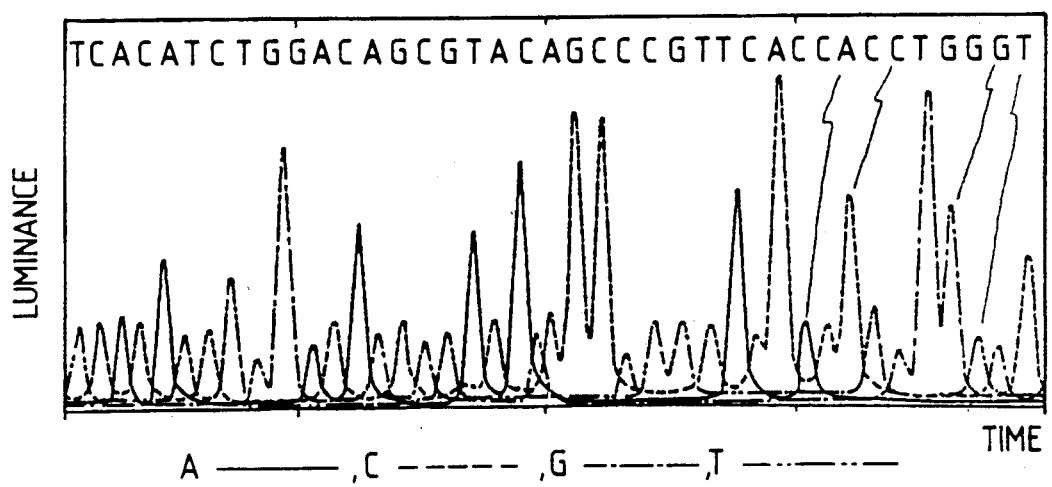
FIG. 3 is a graph illustrating light luminances of four wavelengths varying with time that correspond to four terminal species of DNA fragments.

Referring now to FIGS. 1 through 3, an embodiment of the present invention will be described below.

In FIG. 1, each of four electrophoretic plates 4 has a 3 mm thick slab gel of polyacrylamide of 6% concentration sandwiched mm between two quartz gel supporting plates (not shown) of 300 mm by 200 mm by 5 mm. A DNA analyzed of Ato Inc. is used buffer vessels and power supply. Each electrophoretic plate 4 has 30 sample injection wells of 2 mm wide and 4 mm center intervals (not shown) formed by a comb-like jig in a conventional manner on a top of the slab gel between the gel supporting plates. Each of the electrophoretic plate 4 is vertically oriented on a lower buffer vessel 6 containing buffer. It also has a respective individual upper buffer vessel 5 fixed on one side of a top thereof. Buffer inside the upper buffer vessel 5 is made to supply to the top of the slab gel through an opening on a side thereof (not shown). The upper buffer vessel 5 and the lower buffer vessel 6, as shown in the figure, have a negative electrode and a positive electrode, respectively. A high voltage of 1.2 kV is applied across the electrodes to cause DNA fragments to migrate downward.

The electrophoretic plate 4 has the fluorescence-labeled DNA fragments cut for DNA base sequence determination and injected into the top thereof. It also has a laser beam uniformly thrown on a portion around 25 cm below the top a portion adjacent to the lower end of migration in the slab gel, i.e. a portion adjacent to the bottom of the slab gel.

The DNA fragments labeled with a fluorescence of FITC (fluorescein isothiocyanate) having a 515 nm maximum emission wavelength will migrate on four different migration lanes according to four terminal species, including adenine, cytosine, guanine, and thymine. Each of the DNA fragments that are migrating will emit a fluorescent light when it passes the portion which is irradiated by the laser beam. The fluorescent spectrum lines the number of which is the same as the number of the electrophoretic plates 4, as seen toward a bottom of the lower buffer vessel 6 can be observed. These line images are focused through a filter-equipped lens 7 onto a two-dimensional detector 8 having an image intensifier or a high-sensitivity two-dimensional sensor. As the example has four slab gels, a monitor 12 can display four lines 13 as the line images accordingly.

A fluorescent light luminance of each line, as shown in FIG. 2, changes with time. It can be seen that the fluorescent light luminance changes at portions which correspond to the migration lanes of samples. The two-dimensional sensor can be considered a collection of numbers of line sensors. The information of four line images can be obtained by appropriately processing signals output of the respective line sensors.

Alternatively, the DNA base sequence determination can be made in a way that the DNA fragments are labeled with four fluorophores of different wavelengths corresponding to four respective kinds of terminal species, a condensing lens 7 having a prism (not shown) or the like inserted in front or rear thereof to vertically disperse the fluorescent line images 13 according to the wavelengths, and resultant line images of portions corresponding to the wavelengths of the four fluorophores are appropriately processed. FIG. 3 shows changes of the light luminances of the fluorophores corresponding to the four terminal species with time. From the graphs of the figure, we can know of the time when the DNA fragment group of each terminal species passes the laser beam irradiation portion. Marks A, C, G, and T in FIG. 3 indicate the four terminal species, including the adenine, cytosine, guanine, and thymine, respectively. Characteristic curves represented by a solid line, dotted line, dot-dash line, and two-dot-dash line in the figure indicate changes of light luminances having the wavelengths of the fluorophores corresponding to the marks A, C, G, and T with time. The characteristic curves allows for DNA base sequence determination.

In the example, number of the migration lanes can be made four times as compared with that of the single slab gel. However, the number of the slab gels can be ten or more.

In FIG. 1, numeral 1 indicates a laser beam source, 2 a laser beam, 3 a reflection mirror, 9 a control unit, 10 a data processing unit, 11 a display unit, 16 the lower end of the slab gel.

Second Embodiment

Figure 4:
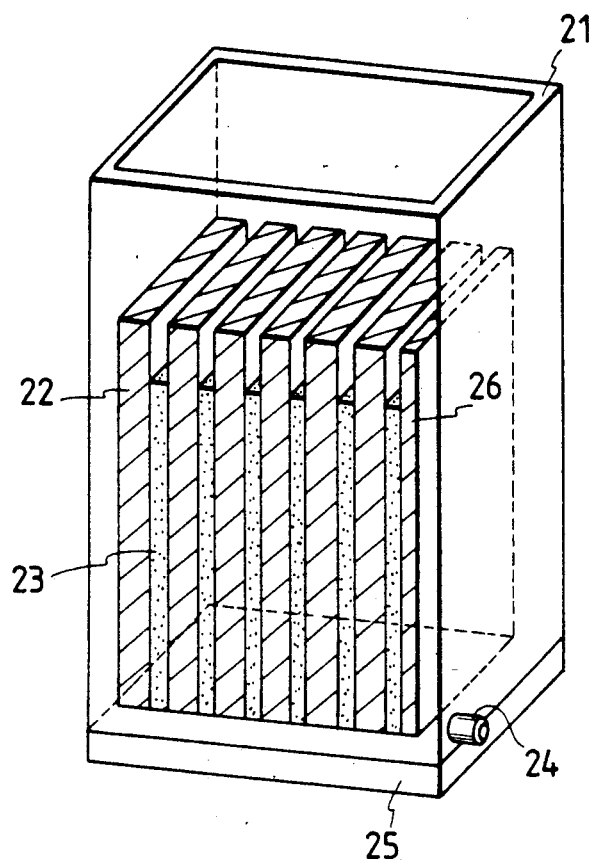
FIG. 4 is a perspective view of a supporting vessel in another embodiment of the fluorescence detection type electrophoresis apparatus of the present invention.
Figure 5:
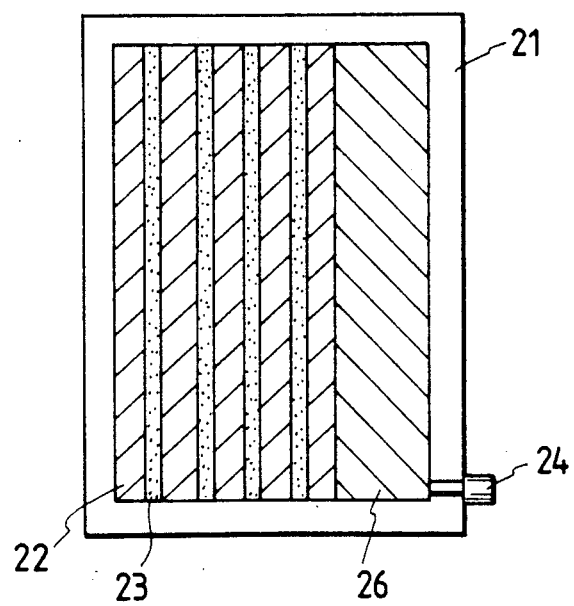
FIG. 5 is a cross-sectional top view of the supporting vessel of FIG. 4.
Figure 6:
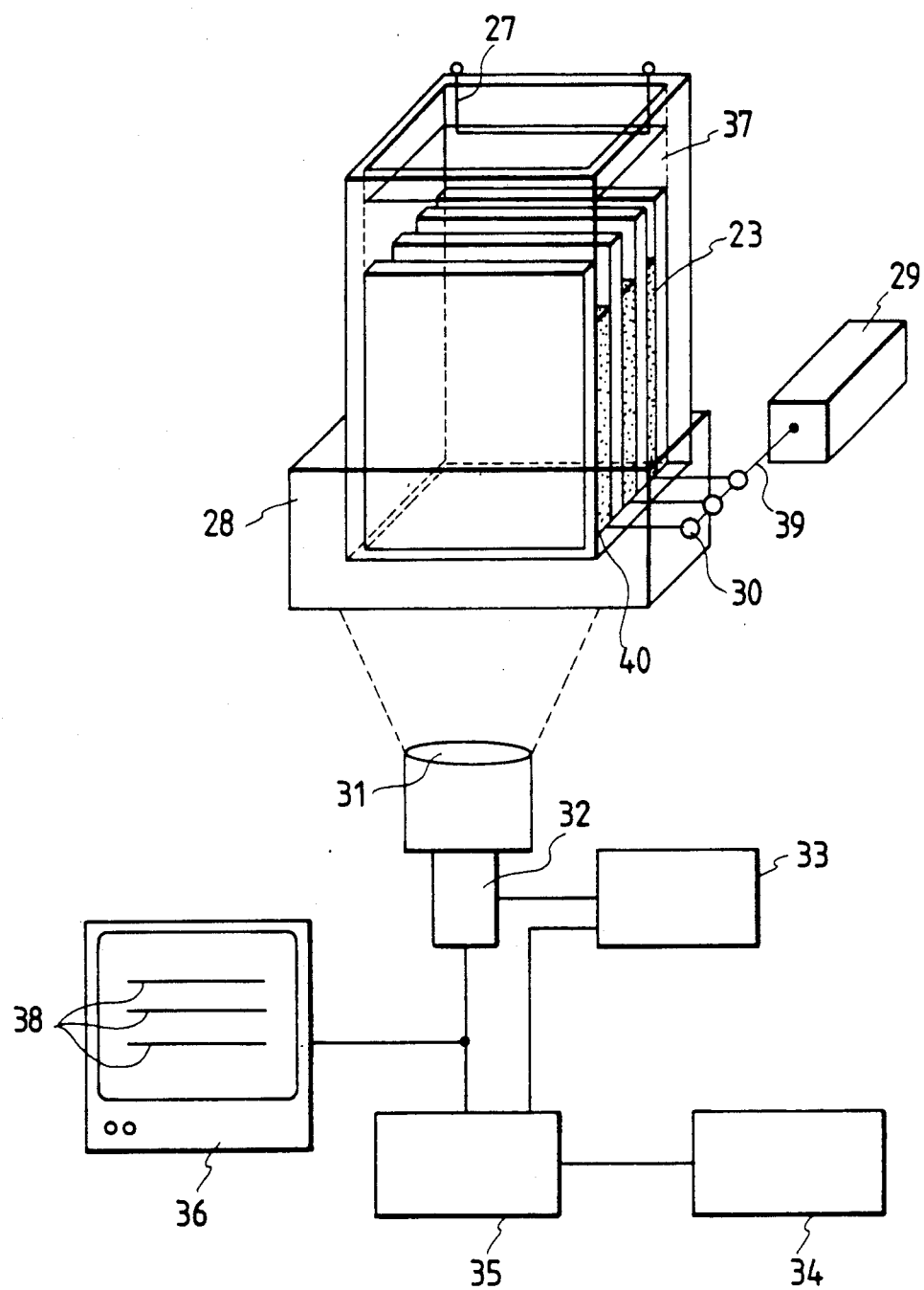
FIG. 6 is a combined block diagram and perspective view of the fluorescence detection type electrophoresis apparatus with the supporting vessel shown in FIG. 4.

Referring now to FIGS. 4 through 6, another embodiment of the present invention will be described below.

In FIG. 4, an electrophoretic plate supporting frame 21 forming a supporting vessel for the fluorescence detection type electrophoresis apparatus of the present invention, inside dimensions of which are 300 mm by 120 mm by 38 mm, and which is made of transparent acrylic resin, has an injection inlet 24 for supplying unpolymerized acrylamide monomer on a lower part thereof. A bottom lid 25 of the electrophoretic plate supporting frame 21 has a communicating groove (not shown) thereon.

Glass plates 22 of 250 mm by 120 mm by 5 mm are arranged at intervals of 0.3 mm inside the electrophoretic plate supporting frame 21 as gel supporting plate. The unpolymerized acrylamide monomer of 4.5% concentration is injected from the injection inlet 24. The unpolymerized acrylamide monomer then flows and is filled in between the glass plates 22 through the communicating groove on the bottom lid 25. In turn, a comb-like jig is put onto slab gels 23 to form 30 sample injection wells of 2 mm wide and 4 mm center intervals (not shown). These are kept at room temperature until the unpolymerized acrylamide monomer is solidified to form the slab gels 23 between the glass plates 22.

FIG. 5 shows top view of laminated slab gel unit formed as described above, whose number of the slab gels is less than the one in FIG. 4. If the number of the slab gels is rather less, then a spacer 26 is inserted in place to prevent the slab gels from changing their position, as shown in the figure. The electrophoretic plate supporting frame 21 has a space on a top thereof so that a buffer solution can be filled therein. Electrodes are connected, and a top lid (not shown) having a vent hole is fitted on the top of the supporting frame. This allows an upper space of the supporting frame to be available as upper buffer vessel. The formed laminated slab gel unit is positioned in a lower buffer vessel 28 as shown in FIG. 6.

On the other hand, fluorescence-labeled DNA fragments are formed in the same manner as in the first embodiment described previously referring to FIG. 1, and are injected into sample injection wells on upper portions of the slab gels. In turn, a 1.0 kV voltage is applied across the upper and lower buffer vessels. This cause the fluorescence-labeled DNA fragments to migrate downward. A measuring system of the fluorescence detection type electrophoresis apparatus shown in FIG. 6 detects fluorescent lights coming out of the DNA fragments.

An argon laser 29 can emit a light 39 of 488 nm wavelength and 10 mW output power. The light 39 is reflected by a mirror divider 30 through a focal lens. The reflected light irradiates the slab gels 23 through the side surface thereof. The light, of course, may be thrown into the buffer solution close to the lower ends of the slab gels to irradiate the DNA fragments coming out of the slab gels. In this case, for example, in forming the slab gels 23, a spacer of a desired height projected on an upper side of the bottom lid is fitted on lower portions of spaces between the glass plates 22 in which the slab gels are formed. The unpolymerized acrylamide monomer is filled in the spaces between the glass plates 22 in which the slab gels are formed in the same way as above, thereby forming the slab gels 23. Thereafter, the bottom lid is replaced by the one having no spacer projected and is fitted in position, and the laser beam is thrown to the lower portions that has no slab gels formed between the glass plates 22. This is advantageous in that without refraction of the laser beam 39 by the slab gels, the laser beam 39 need not be divided, but only reflected by the mirror, allowing the irradiation to be made on all the lower ends of the slab gels. Then, the line images emitting fluorescent lights can be observed at the lower end of the laminated slab gel unit. The fluorescent images are focused through a filter-equipped lens 31 on a high-sensitivity two-dimensional sensor 32 of Hamamatsu Photonix Inc. If three sheets of slab gels are provided, a monitor 36 can display three fluorescent images 38.

In FIG. 6, numeral 27 indicates an electrode, 33 a controller, 34 a display unit, 35 a data processing unit, 37 a buffer solution, and 40 the migration directed lower end of the slab gel.

As clearly understood from the description above, the fluorescence detection type electrophoresis apparatus of the present invention provides an increased processing capability of fluorescent detection in that a single measuring system can obtain information from numbers of electrophoretic plates at the same time, that number of migration lanes capable of processing samples can be increased in propotion to the number of slab gels. The apparatus therefore can quickly perform fluorescent detection of numbers of samples for DNA base sequence determinations of numbers of DNA fragments, such as in analysis of human genes.

Also, the fluorescence detection type electrophoresis apparatus of the invention is capable of forming numbers of slab gels in a simple way that unpolymerized acrylamide monomer is injected into the supporting vessel containing the gel supporting plates.

What is claimed is:

1. A fluorescence detection type electrophoresis apparatus comprising:
   a plurality of slab gels arranged substantially parallel to each other, said slab gels providing a plurality of migration lanes along which sample fragments labeled with fluorophore migrate from upper ends toward lower ends of the slab gels;
   an upper buffer vessel containing a buffer solution in contact with the upper ends of said slab gels;
   a lower buffer vessel containing a buffer solution in contact with the lower ends of said slab gels;
   means for providing electric potential between said buffer solution in said upper buffer vessel and buffer solution in said lower vessel to provide electrophoretic force to said sample fragments on said migration lanes;
   excitation means for exciting the sample fragments labelled with fluorophore and existing in the migration lanes of said slab gels, each migration lane being positioned adjacent to one of said lower ends of said slab gels; and
   means for individually and simultaneously detecting fluorescent lights emitted from the sample fragments labelled with fluorophore in said migration lanes and emitting from the lower ends of said slab gels.

2. A fluorescence detection type electrophoresis apparatus according to claim 1, in which a bottom portion of said lower buffer vessel is transparent and said means for detecting fluorescent lights detects fluorescent lights emitted from said bottom portion of said lower buffer vessel.

3. A fluorescence detection type electrophoresis apparatus according to claim 2, wherein said means for detecting fluorescent lights comprises:
   i) a two-dimensional fluorescent light detector having a light receiving surface situated along the path of the fluorescent light emission; and
   ii) a lens disposed between said bottom portion of said lower buffer vessel and said light receiving surface, said lens focuses on said light receiving surface a plurality of line-shaped fluorescent light images formed of fluorescent lights emitted from said lower ends of said slab gels.

4. A fluorescence detection type electrophoresis apparatus according to claim 3, in which said electrophoresis apparatus further comprises a wavelength dispersion means disposed between said lens and said bottom portion or between said lens and said light receiving surface, said wavelength dispersion means dispersing, by wavelength, said plurality of line shape fluorescent light images formed of fluorescent lights coming out from said lower ends of said slab gels.

5. A fluorescence detection type electrophoresis apparatus according to claim 1, in which said plurality of the slab gels are integrated together by gel supporting plate means.

6. A fluorescence detection type electrophoresis apparatus according to claim 1, in which said electrophoresis apparatus is a separation and detection apparatus for DNA or RNA.

7. A fluorescence detection type electrophoresis apparatus comprising:
   a plurality of slab gels arranged substantially parallel to each other, providing a plurality of migration lanes along which sample fragments labeled with fluorophore migrate from upper ends of said slab gels toward lower ends of said slab gels;
   means for providing electrophoretic force to the sample fragments on said migration lanes;
   means for irradiating the sample fragments labelled with fluorophore, said irradiating means irradiating along the lower side edge portion of said slab gels, wherein fluorescent lights emit from said lower ends of said slab gels;
   a two-dimensional light detector having a light receiving surface positioned along the path of the fluorescent lights emission; and
   a lens system disposed between said lower ends of said slab gels and said receiving surface of the light detector, said lens system focusing on a plurality of line-shaped fluorescent light images produced by the fluorescent lights emitted from said lower ends of said slab gels on said light receiving surface.

8. A fluorescence detection type electrophoresis apparatus comprising:
   a plurality of slab gels arranged substantially parallel to each other, each providing a plurality of migration lanes along which sample fragments labeled with fluorophore migrate from upper ends of said slab gels toward lower ends of said slab gels,
   means for providing electrophoretic force to the sample fragments on said migration lanes,
   excitation light source projecting a plurality of excitation light beams respectively on said slab gels from side ends of the slab gels through respective migration lanes to excite the sample fragments labelled with fluorophore existing in said migration lanes, each of said light beam crossing said migration lanes provided in each of said slab gels at a position adjacent to each of the lower ends of said slab gels; and means for individually and simultaneously detecting fluorescent lights emitted from the fluorophore in said migration lanes and emitted from the lower ends of said slab gels.

9. A fluorescence detection type electrophoresis apparatus according to claim 8, in which said means for detecting fluorescent lights comprises:

a two-dimensional light detector having a light receiving surface positioned along the path of the fluorescent light emission; and a lens system disposed between said lower ends of said slab gels and said receiving surface of the light detector, said lens focusing a plurality of line-shaped fluorescent light images produced by fluorescent lights emitted from said lower ends of said slab gels on said light receiving surface.

* * * * *